(12) United States Patent
McLaughlin

(10) Patent No.: US 11,857,393 B2
(45) Date of Patent: Jan. 2, 2024

(54) INTERNAL BONE FIXATION DEVICE

(71) Applicant: Amplify, Inc., Scarborough, ME (US)

(72) Inventor: Brian R. McLaughlin, Yarmouth, ME (US)

(73) Assignee: ALM Ortho, Inc., Woolwich, ME (US)

( * ) Notice: Subject to any disclaimer, the term of this patent is extended or adjusted under 35 U.S.C. 154(b) by 0 days.

(21) Appl. No.: 16/822,852

(22) Filed: Mar. 18, 2020

(65) Prior Publication Data
US 2020/0297505 A1   Sep. 24, 2020

Related U.S. Application Data

(60) Provisional application No. 62/820,308, filed on Mar. 19, 2019.

(51) Int. Cl.
*A61F 2/44* (2006.01)
*A61F 2/30* (2006.01)

(52) U.S. Cl.
CPC ..... *A61F 2/447* (2013.01); *A61F 2002/30112* (2013.01); *A61F 2002/30971* (2013.01)

(58) Field of Classification Search
CPC ........ A61F 2/44; A61F 2002/44; A61F 2/447; A61F 2/4455; A61F 2/446; A61F 2/4465
See application file for complete search history.

(56) References Cited

U.S. PATENT DOCUMENTS

| | | | |
|---|---|---|---|
| 2007/0100450 A1* | 5/2007 | Hodorek | A61L 27/52 623/14.12 |
| 2008/0004704 A1* | 1/2008 | Katz | A61F 2/442 623/17.16 |
| 2008/0306609 A1* | 12/2008 | Lee | A61B 17/72 623/23.58 |
| 2009/0118836 A1* | 5/2009 | Cordaro | A61F 2/442 623/17.16 |
| 2019/0343644 A1* | 11/2019 | Ryan | A61F 2/30771 |
| 2023/0285159 A1* | 9/2023 | Chevalier | A61F 2/4611 623/17.11 |

* cited by examiner

*Primary Examiner* — Matthew J Lawson

(57) ABSTRACT

An internal bone fixation device that includes a support frame that is strong but able to absorb compressive forces and that surrounds a porous architecture that helps facilitate bone fusion.

13 Claims, 16 Drawing Sheets

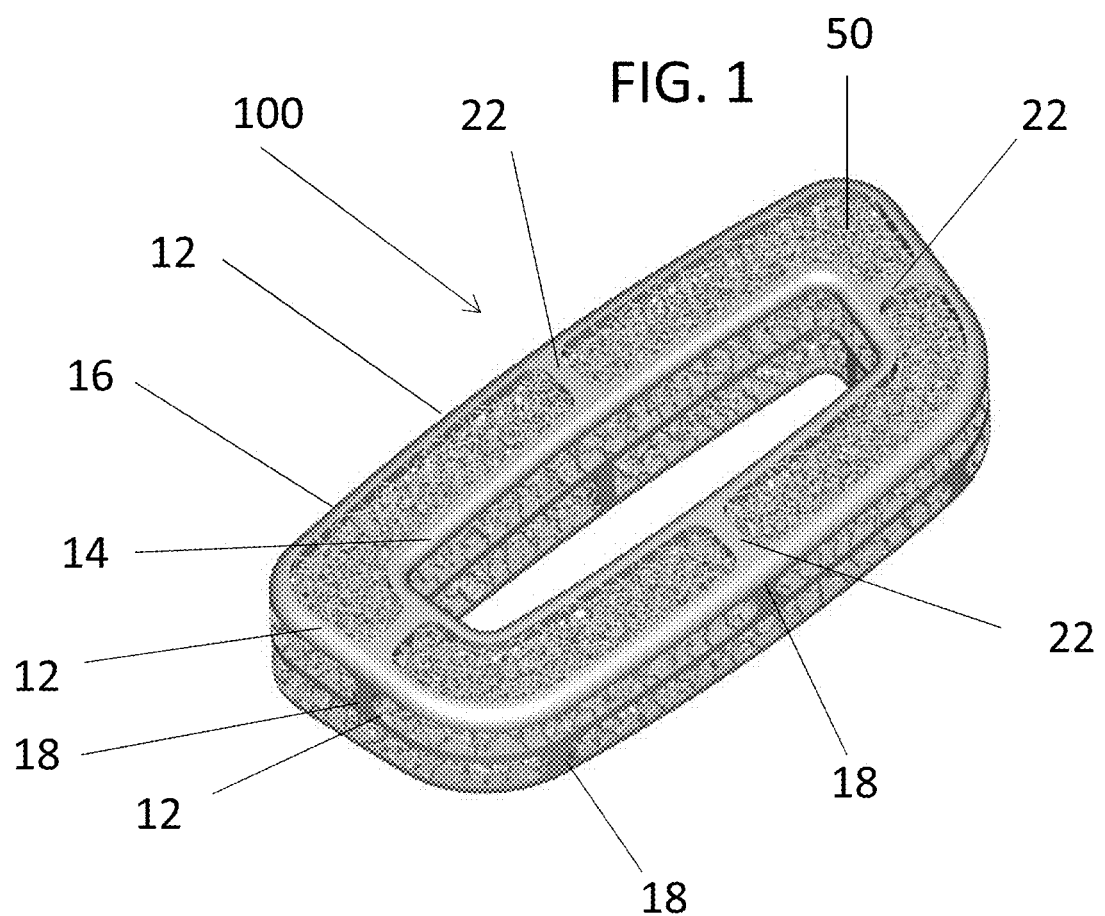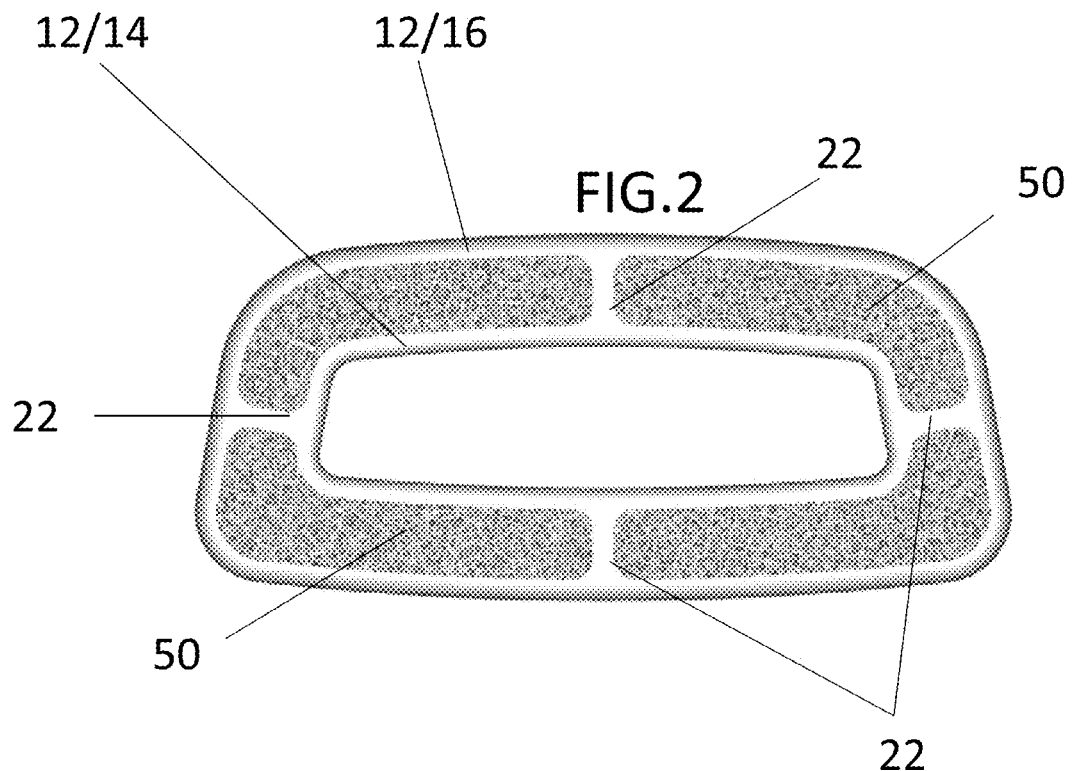

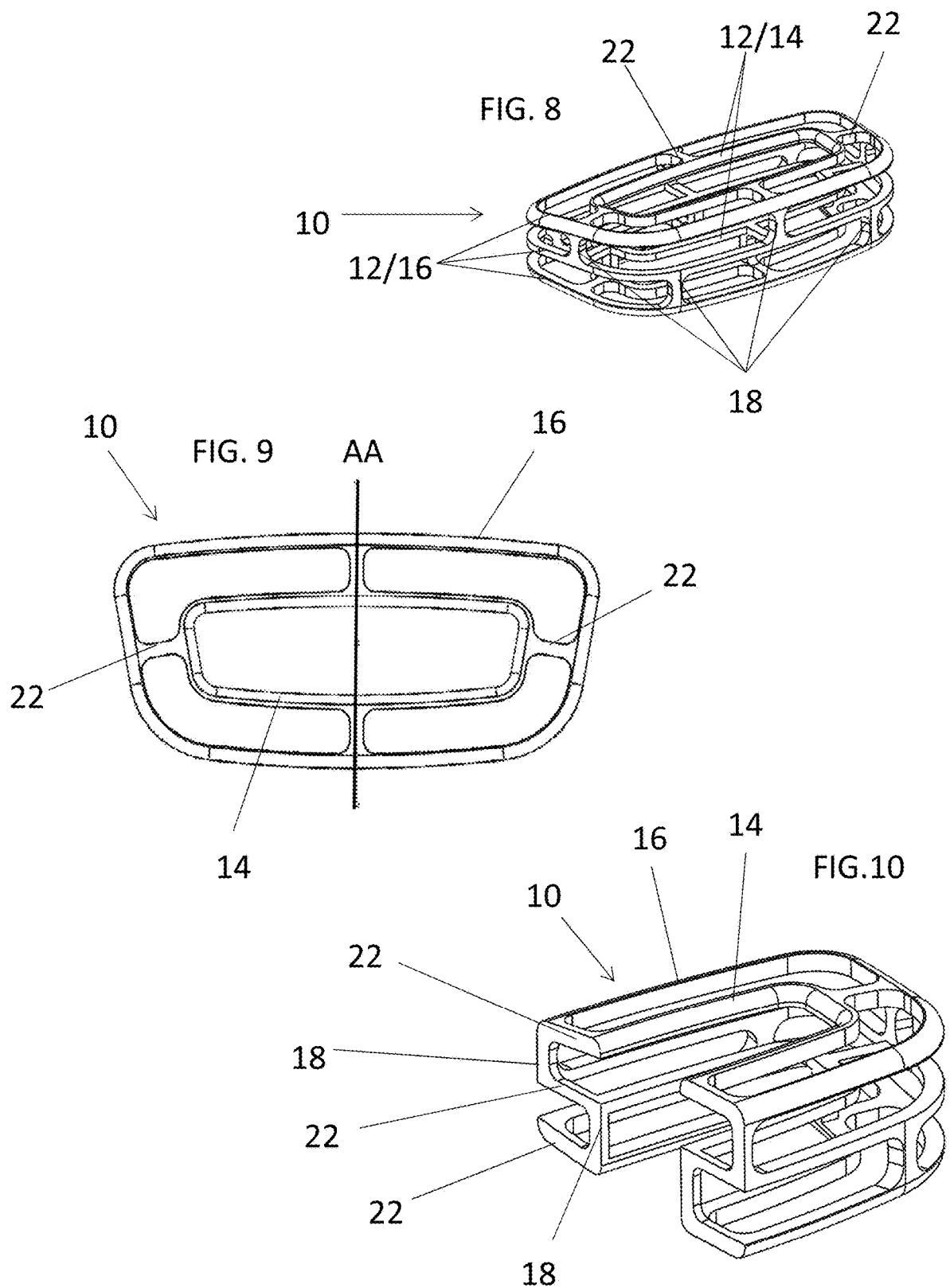

50

50

50

50

INTERNAL BONE FIXATION DEVICE

BACKGROUND INFORMATION

Field of the Invention

The present invention relates generally to medical devices and, more specifically, to implants that aid bone fusion in the body.

Discussion of Prior Art

Internal bone fixation devices, or implants, are used in humans and animals to support and/or secure the subject's bones. For example, implants are used in the spine to support and/or replace damaged tissue between the vertebrae in the spine. Once implanted between two vertebrae, the implant provides support between the two vertebrae and bone growth takes place around and through the implant to at least partially fuse the two vertebrae for long-term support.

Implants often include relatively large rims comprised of solid material that may cover, for example, 50% of the area that interacts with the endplate. The rim may provide a contact area between the implant and the vertebral end plates. However, these large rims have several drawbacks. For example, large rims often impede bone growth and reduce the size of the bone column fusing the superior and inferior vertebral bodies.

Spinal implants typically include open channels through the center of the supporting rims in a superior/inferior direction. The open channel design requires members of the implant that separate the rims that interact with the vertebral endplates to absorb the compressive forces between the vertebral end plates. This often increases the pressure on smaller areas of the vertebral endplates and may potentially lead to stress risers in the vertebral endplates. Further, while bone graft material is often used in conjunction with implants to encourage bone growth, the open column design of implants may reduce the likelihood of bone graft material from securing itself to the implant which may result in a bio-mechanical cooperation that is not conducive to promoting good fusion.

Bone graft material may be packed into the implant in a high-pressure state to prevent bone graft material from exiting the implant while being placed between the vertebral endplates. The high-pressure state may also reduce the potential for the bone graft material loosening due to motion between the implant and the vertebral endplates or compressive forces experienced during settling of the implant. In addition, a high-pressure environment may allow the bone graft material to re-model and fuse at greater strength. High pressure states, however, may be difficult to create and maintain for the bone graft material in an implant.

What is needed, therefore, is an implant that has a rim that minimizes the effects of bone growth impediment while having the strength and flexibility to comfortably and safely absorb the compressive forces that occur as the subject moves about in the normal course of daily activities.

BRIEF SUMMARY OF THE INVENTION

The invention is multi-layer implant device for interfacing with a bone structure that uses a number of off-setting struts to connect the layers, with a porous material filling the internal portion of the device structure between the layers. Each layer includes an inner rim and an outer rim that are connected to one another by horizontal struts, with the inner rims creating an open channel in the center of the device. More specifically, the device includes at least three, and possibly more, layers that are connected by non-continuous vertically oriented offsetting struts.

The non-continuous vertically oriented struts are offset from one another in that one pair of layers are connected by struts connecting the inner rim while a next pair of layers are connected by struts connecting the outer rims, i.e., if the first and second layers are connected at the inner rims the second and third layers are connected at the outer rims. The offsetting strut alignment allows for the use of a comparatively small rim and yet still provides the device with a strong frame but also provides the device with a degree of flexibility or elasticity that allows it to absorb the compressive forces that are exerted on it as the body in which it is implanted moves.

For example, the device may be used in the spine to support and/or replace damaged tissue between the vertebrae. Once implanted between two vertebrae, the implant may provide support between the two vertebrae and bone growth may take place around and through the implant to at least partially fuse the two vertebrae for long-term support. As a person moves about, for example walking or jogging, compressive forces act on the insert which the device is able to absorb.

The inner rims form an open channel in the center of the device, and collectively the layers of inner rims and outer rims define the structure that contains the porous materials. The combination of relatively small, e.g. narrow, rim members and the porous architecture create an ideal area for bone growth.

The device may be sized and shaped to fit into a number of areas of the body. For example, it may be shaped similar to a rounded rectangle or a trapezoid having rounded edges, which may be particularly well suited for a spinal implant. Or, alternatively, the device may be roughly cylindrical in shape in which case it may be used as a mid-shaft implant for a long bone such as the femur.

BRIEF DESCRIPTION OF DRAWINGS

The present invention is described with reference to the accompanying drawings. In the drawings, like reference numbers indicate identical or functionally similar elements. The drawings are not drawn to scale.

FIG. 1 is a perspective view of the device according to the invention showing the top, front, and side.

FIG. 2 is a top plan view of the device.

FIG. 8 is a perspective view of the device frame without the porous architecture showing the top, front, and side.

FIG. 9 is a top view of the frame.

FIG. 10 is a perspective cross-sectional along the line AA in FIG. 9.

DETAILED DESCRIPTION OF THE INVENTION

The present invention will now be described more fully in detail with reference to the accompanying drawings, in which the preferred embodiments of the invention are shown. This invention should not, however, be construed as limited to the embodiments set forth herein; rather, they are provided so that this disclosure will be complete and will fully convey the scope of the invention to those skilled in the art.

FIGS. 1-29 illustrate an internal bone fixation device 100 according to the invention. The device may be suitable for use with any number of implant situations, such as long bone reconstruction, knee replacements, both anterior lumbar inter-body fusion and posterior lumbar inter-body fusion, as well as with the foot and ankle. The following disclosure largely discusses the internal bone fixation device 100, which may also simply be referred to as an "implant," in terms of its use with lumbar inter-body fusion, however, it is understood that this is only one example of use and is not limiting in any way. The embodiment shown in FIGS. 1-15 is particularly advantageous for use as a lumbar interbody fusion device, while the embodiment shown in FIGS. 26-29 is particularly advantageous as a mid-shaft implant for a long bone.

The internal bone fixation device 100 according to the invention includes a support frame 10 that bounds and surrounds a porous architecture 50. Generally, the frame is shaped to match the shape of the bone regions in which the device 100 is used for fusion, with approximate geometric shapes ranging from rounded and oval, rectangular or trapezoidal, or rounded rectangles and trapezoids having rounded edges. Generally, any corners are rounded so as to reduce the risk of harming other parts of the body during insertion.

Figure 3:
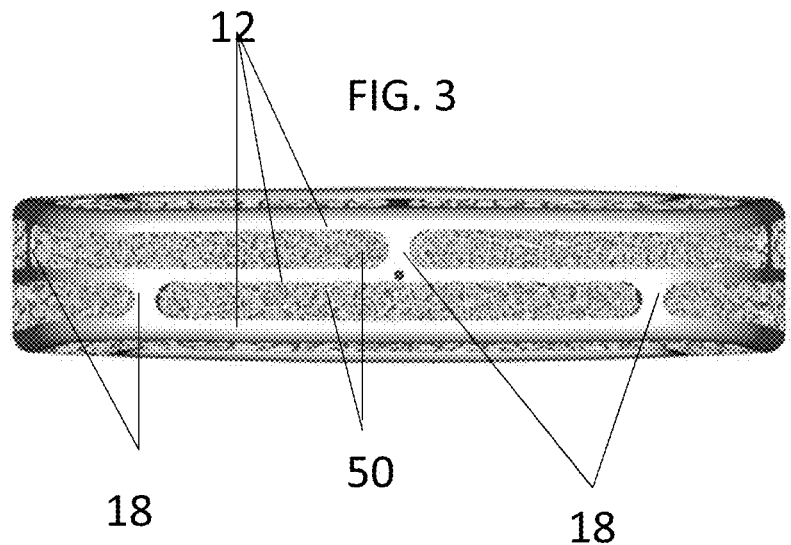
FIG. 3 is a right side view of the device.
Figure 4:
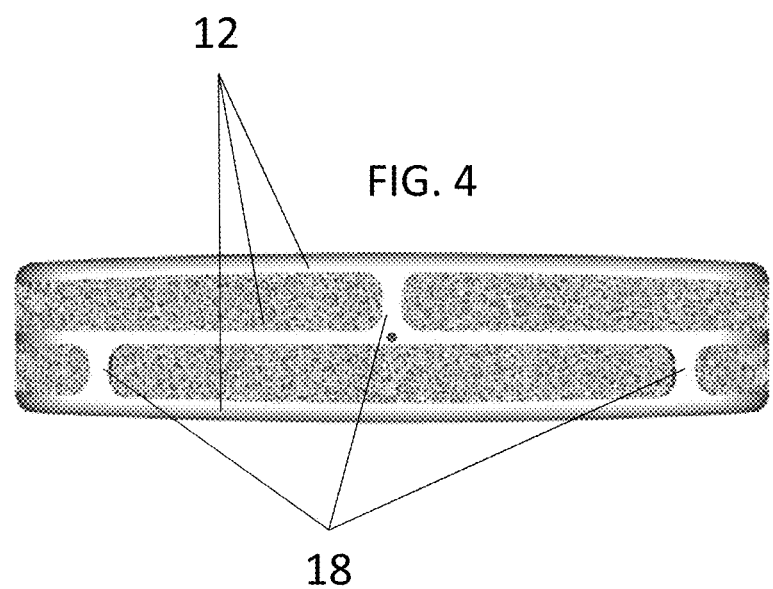
FIG. 4 is a left side view of the device.
Figure 5:
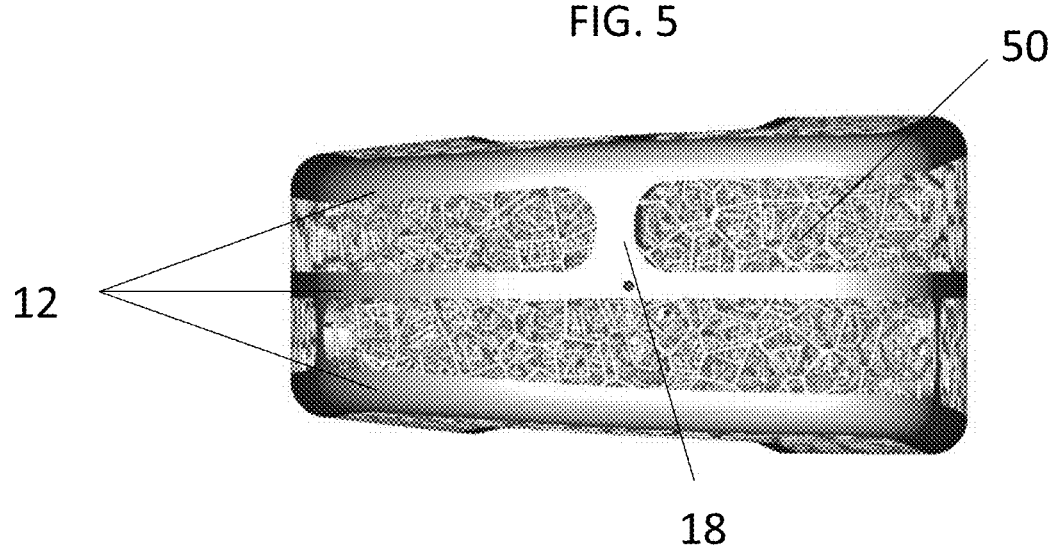
FIG. 5 is an end view of the device.
Figure 6:
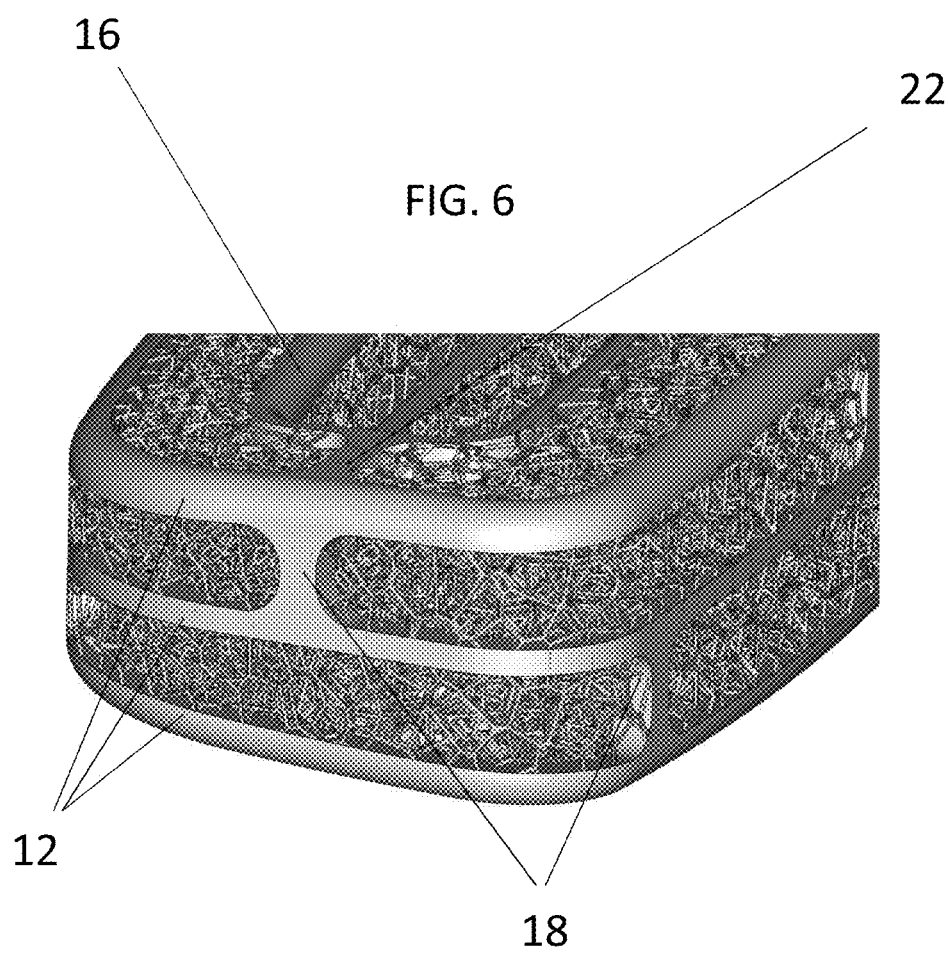
FIG. 6 is a perspective view showing the top and end of the device.
Figure 7:
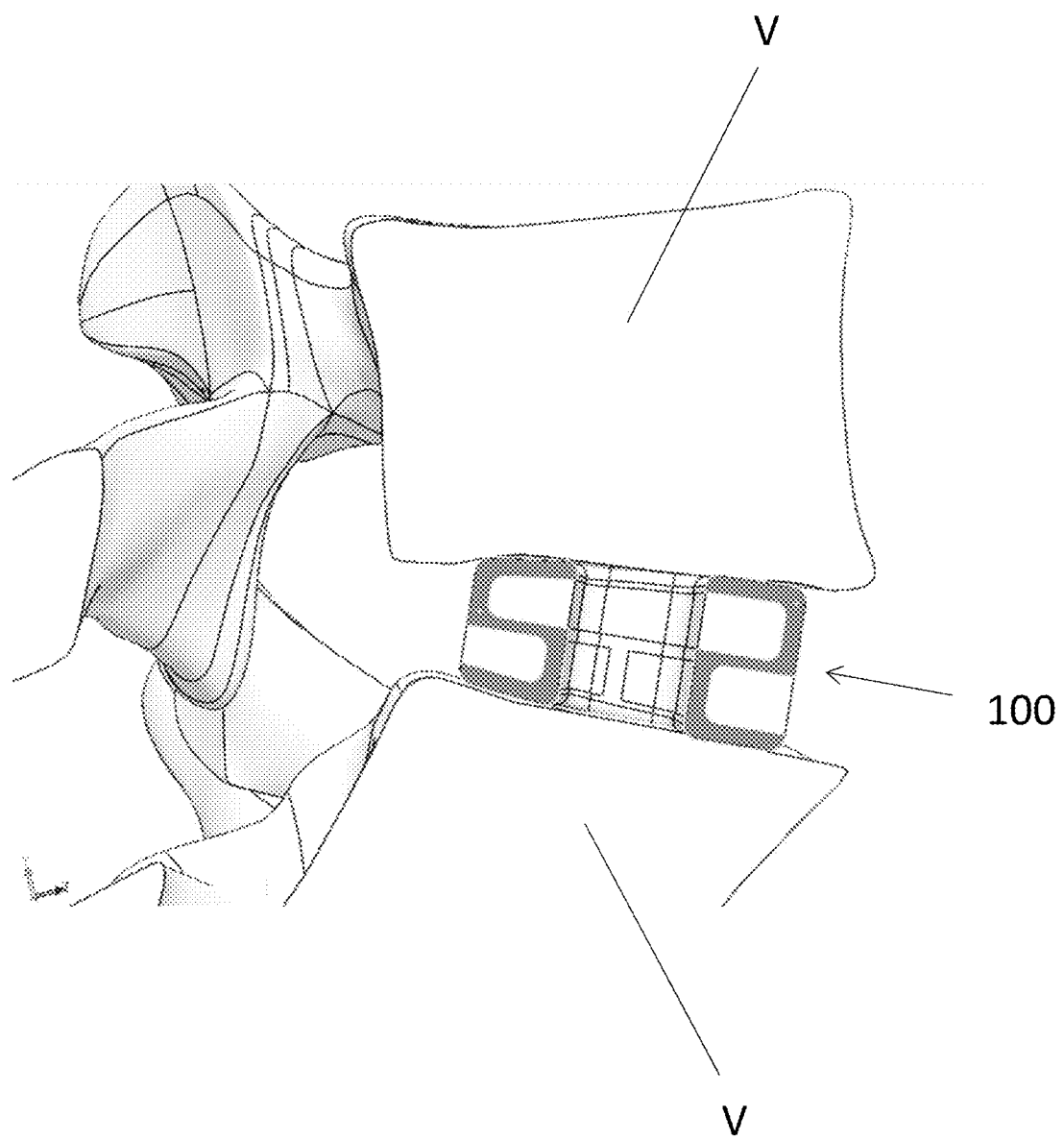
FIG. 7 is a side view of the device inserted between two vertebras.
Figure 11:
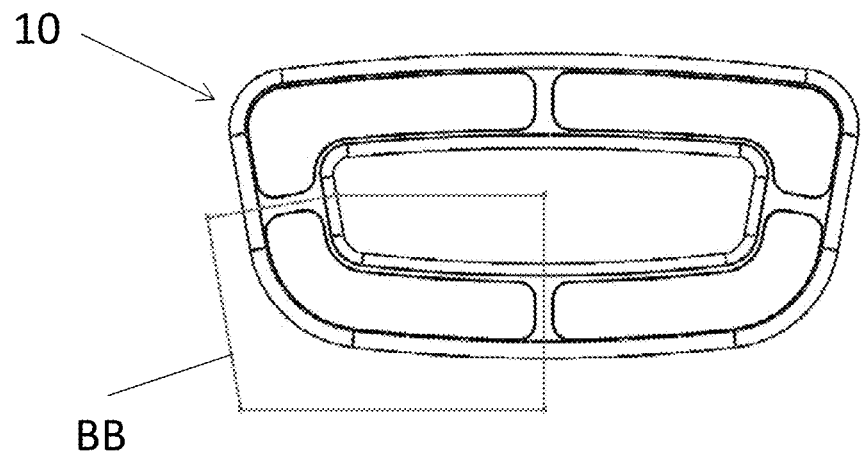
FIG. 11 is a top view of the frame.

FIGS. 1-16 illustrate the first embodiment of the device 100, in which the frame 10, best illustrated by FIGS. 8-12, includes three layers 12. Each layer 12 includes an inner rim 14 and an outer rim 16. The layers 12 are connected to one another by a first set of struts 18, and the inner rims 14 and outer rims 16 are connected to one another by a second set of struts 22. Additional layers 12 may be added in a similar manner to create a larger version of the device. FIG. 7 illustrates one use of the first embodiment of the device 100, with the device 100 inserted into the disc space between two vertebra V.

The outer rim 16 and inner rim 14 in this first embodiment generally have a shape that is approximately in the form of an oval or a rectangle or trapezoid with slightly rounded edges, which is generally intended to be the shape of device needed for lumbar interbody fusion. One side of each rim 14, 16, is slightly narrower than the other. The layers are separated by approximately the same distance from one another, with the layers 12 on side of the device 100 tapered inward slightly. The angle and curvature of the device 100 is intended to match the Lordotic Angle of the area of the spine where the implant is intended to be inserted. The inner rim 14 bounds and defines an open channel through the center of the device. Again, as previously noted, the overall size and/or shape of the device 100 may vary to correspond to the size and/or shape of the cross section of the bones at the fusion or osteotomy site, thereby providing an optimal environment for bone ingrowth to occur.

The outer surfaces of the device 100, and in particular the outer surface of the outer rim 16, may be substantially smooth and/or be polished so as to limit the risk of damaging internal body structures as the device is being inserted. Alternatively, or in addition, some portion of the outer surface may also be roughened to facilitate bone fusion and/or interactions with other materials. The device may be made of any suitable medical grade material such as, for example, titanium or a biocompatible polymer.

Figure 12:
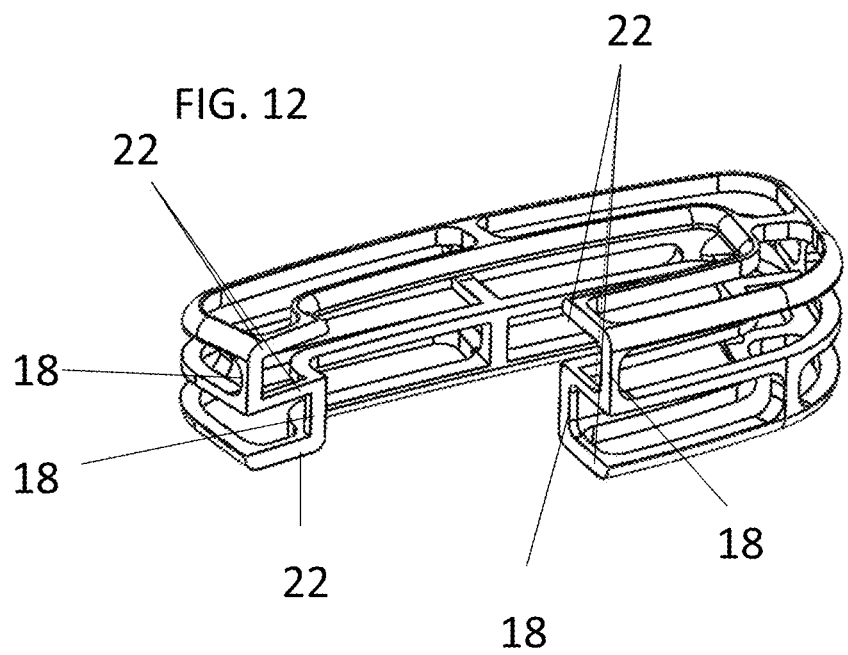
FIG. 12 is a perspective cross-sectional along the line BB in FIG. 11.
Figure 13:
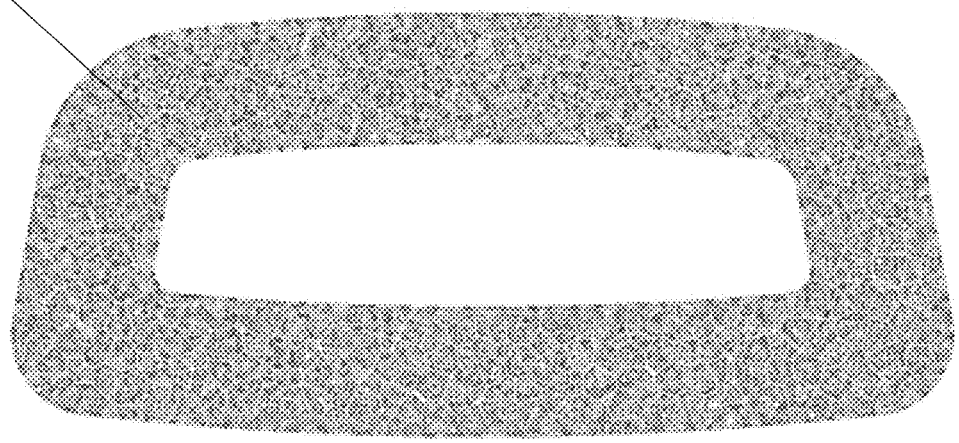
FIG. 13 is a top view of the porous architecture.
Figure 14:
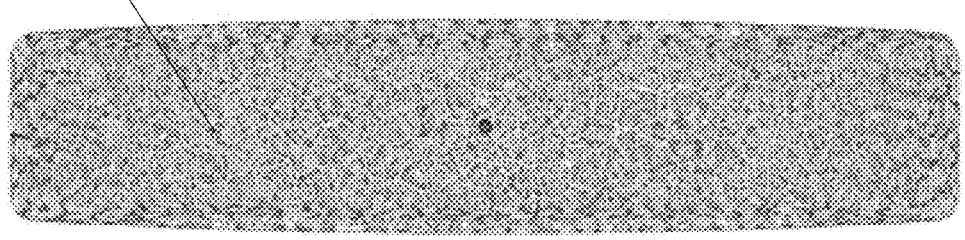
FIG. 14 is a side view of the porous architecture.
Figure 15:
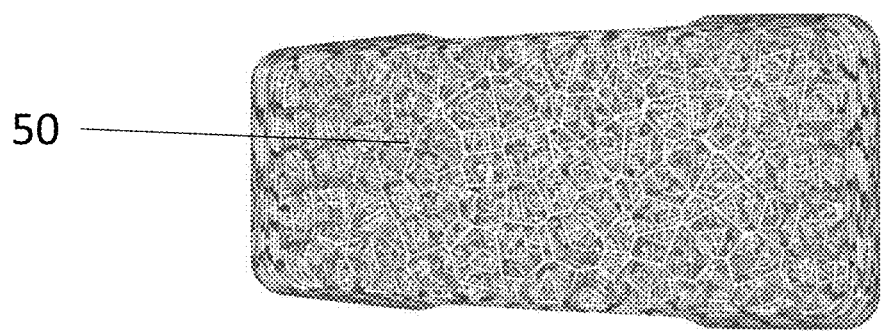
FIG. 15 is an end view of the porous architecture.
Figure 16:
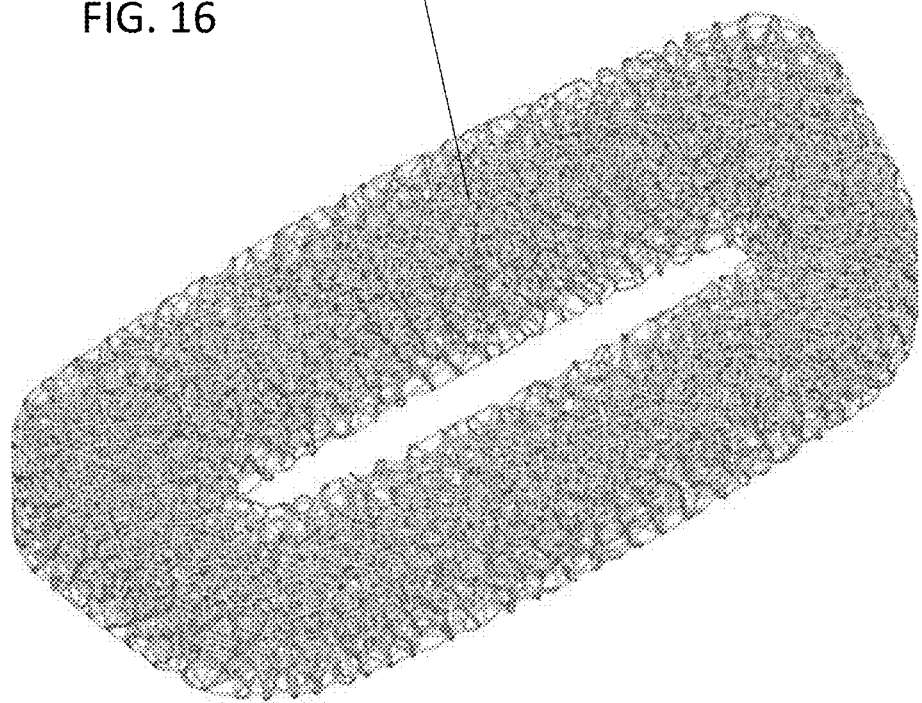
FIG. 16 is a perspective view of the porous architecture.
Figure 17:
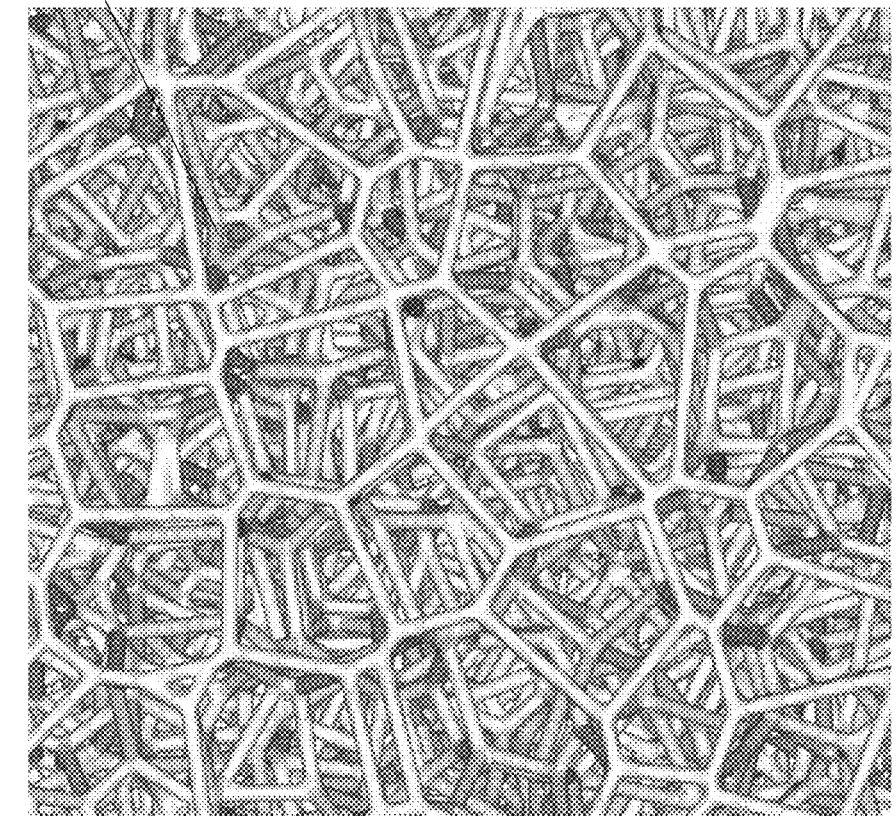
FIG. 17 is a close up view of a portion of the porous architecture.
Figure 18:
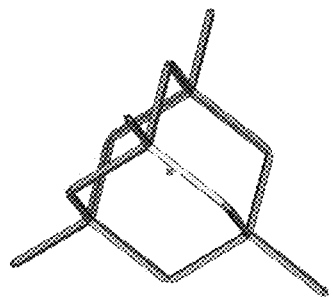
FIG. 18 illustrate once example of a strand connection that may be used to create the porous architecture.
Figure 19:
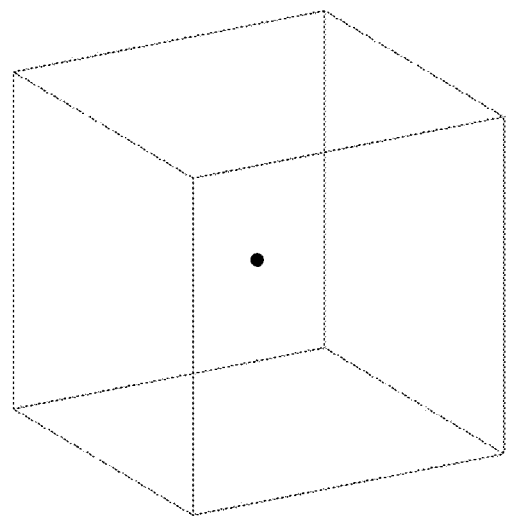
FIG. 19 illustrate where the strand shown in FIG. 17 may fit into the largely porous material.
Figure 20:
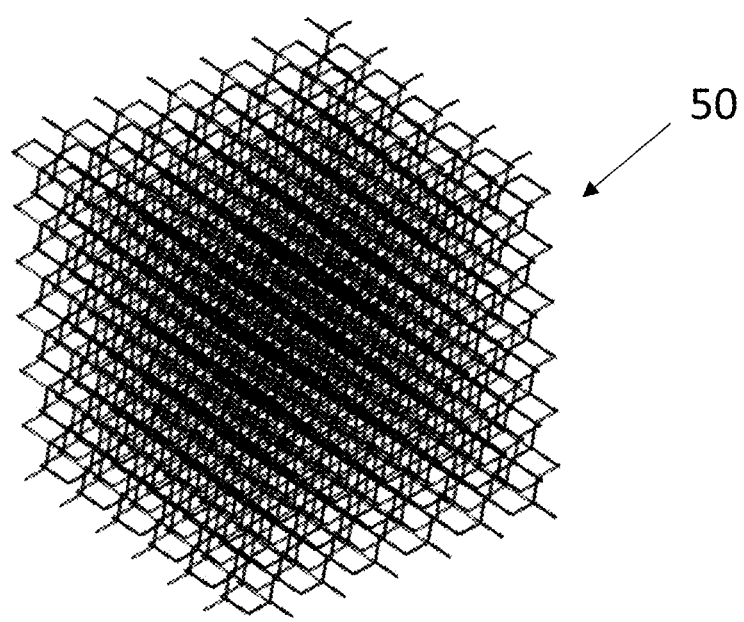
FIG. 20 illustrates a first example of a porous architecture.
Figure 21:
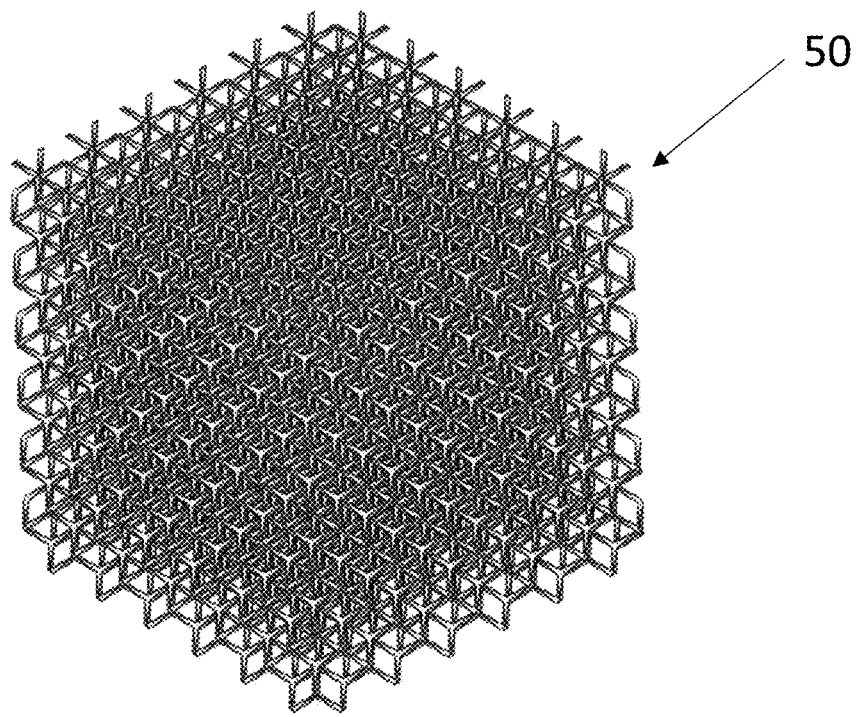
FIG. 21 illustrates a second example of a porous architecture.
Figure 22:
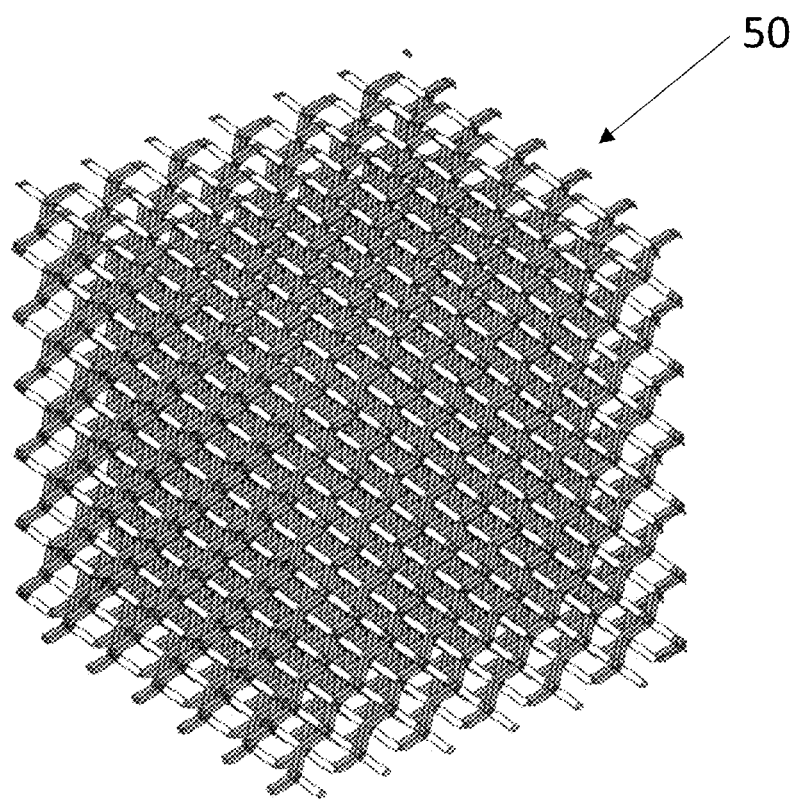
FIG. 22 illustrates a third example of a porous architecture.

The first set of struts 18 are connected to the layers 12 in an offsetting manner, which is to say that the first and second layers are connected to one another by struts 18 that are attached to the outer rims 16 while the second and third layers are connected to one another by struts 18 that are attached to the inner rims 14. If viewed from the cross-sectional side view, as shown in FIGS. 10 and 12, this offsetting arraignment forms an approximate S-shape. When adding additional layers, it is preferred if the total number of layers is an odd number so that the same three-layer strut arrangement may be maintained throughout the additional layers.

The distance between the individual struts in the first set of struts 18 may vary. For example, an implant that is designed to be used with a human spine may measure approximately 50 millimeters ("mm") wide, 25 mm deep and 12 mm in height. In this example, the individual struts in the first set of struts 18 may be spaced approximately 15 mm apart. Changing the spacing, or incorporating more or fewer struts, alters the strength and flexibility of the device at various points. As previously noted, the size and/or shape of the device may vary to correspond to the size and/or shape of the cross section of the bones at the fusion or osteotomy site.

FIGS. 13-22 illustrate the porous architecture 50. The porous architecture 50 may be any architecture that includes a plurality of openings on an outer surface of the architecture such that these openings may contact a bone surface. It is advantageous if there are openings or spaces throughout the porous architecture so that bone is able to grow into and throughout the porous architecture. The porous architecture may be a lattice or matrix structure that is configured to allow, promote or encourage bone to grow into it and around it. The porous architecture may be mostly comprised of a uniform or mostly uniform non-variable arrangement. Conversely, the porous architecture may be comprised of any number of suitable patterns, such as a plurality of diamond or square shapes trusses or in the form of a honeycomb. It may also be a randomly generated or distributed architecture or lattice, or it may include a different architecture in differing portions. The only requirement of the porous architecture is that it has openings or spaces that contact a bone segment.

Figure 23:
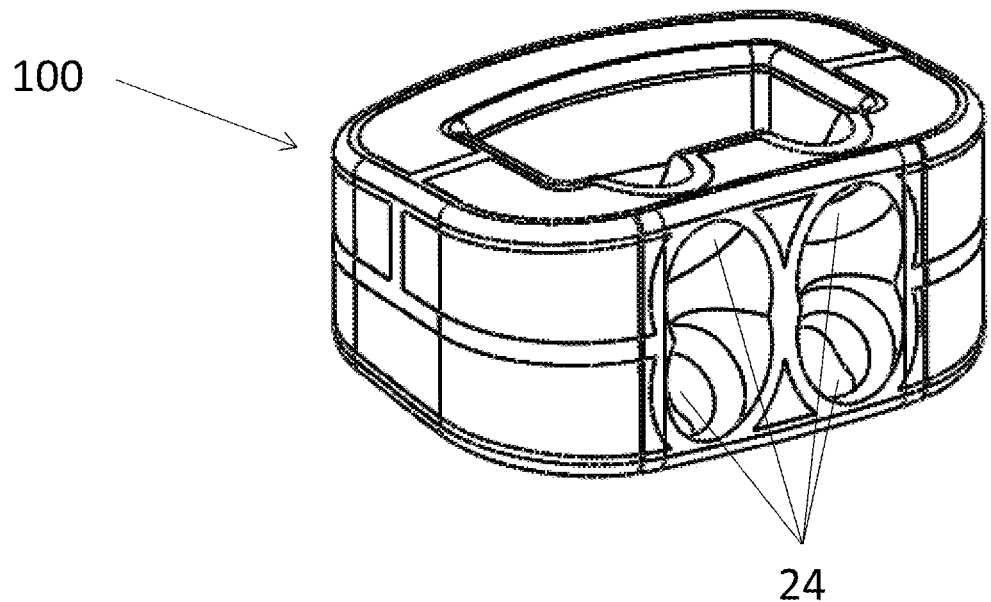
FIG. 23 is a perspective view of the device having apertures for threaded fasteners.
Figure 24:
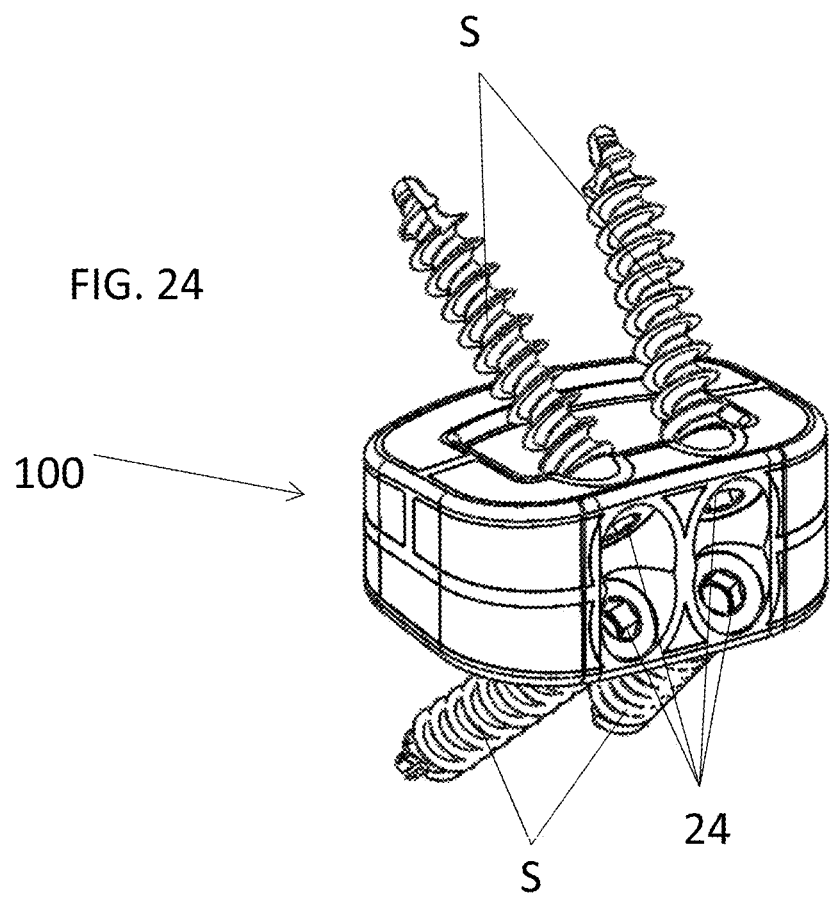
FIG. 24 is a perspective view of the device having threaded fasteners.
Figure 25:
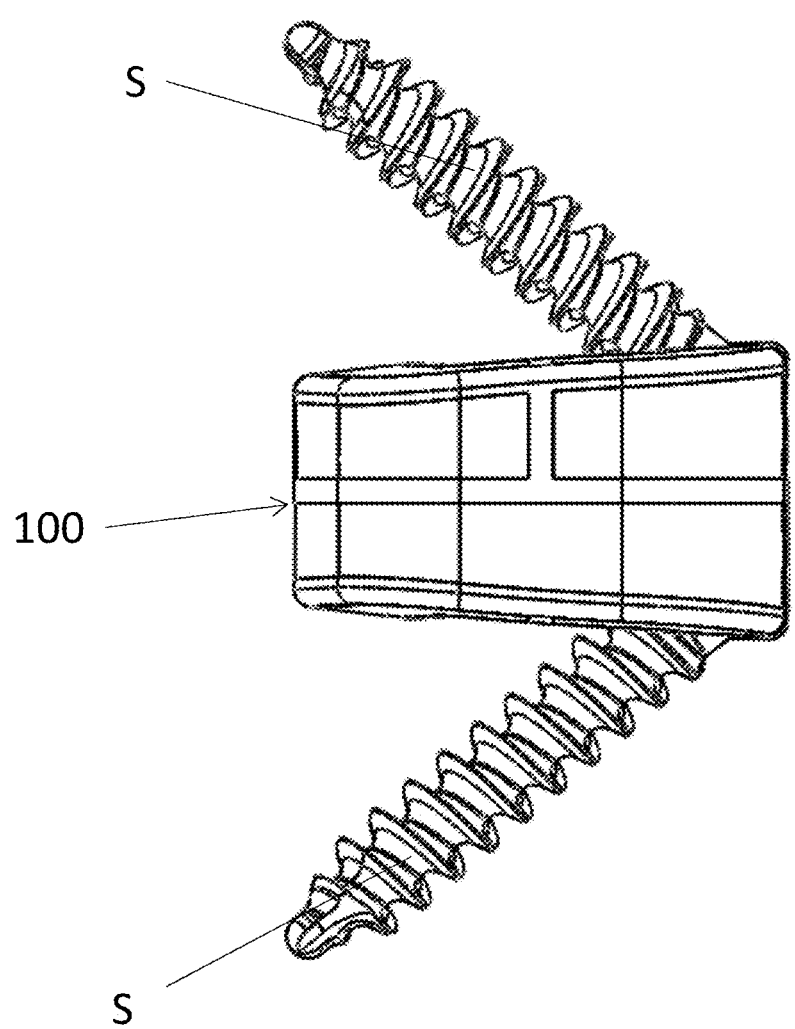
FIG. 25 is an end view of the device with threaded fasteners.

The device may be affixed to the bone using conventional attachment means such as a plate or fastening devices such as screws. FIGS. 23-25 illustrate an embodiment of the device having apertures 24 for the insertion of screws S.

Figure 26:
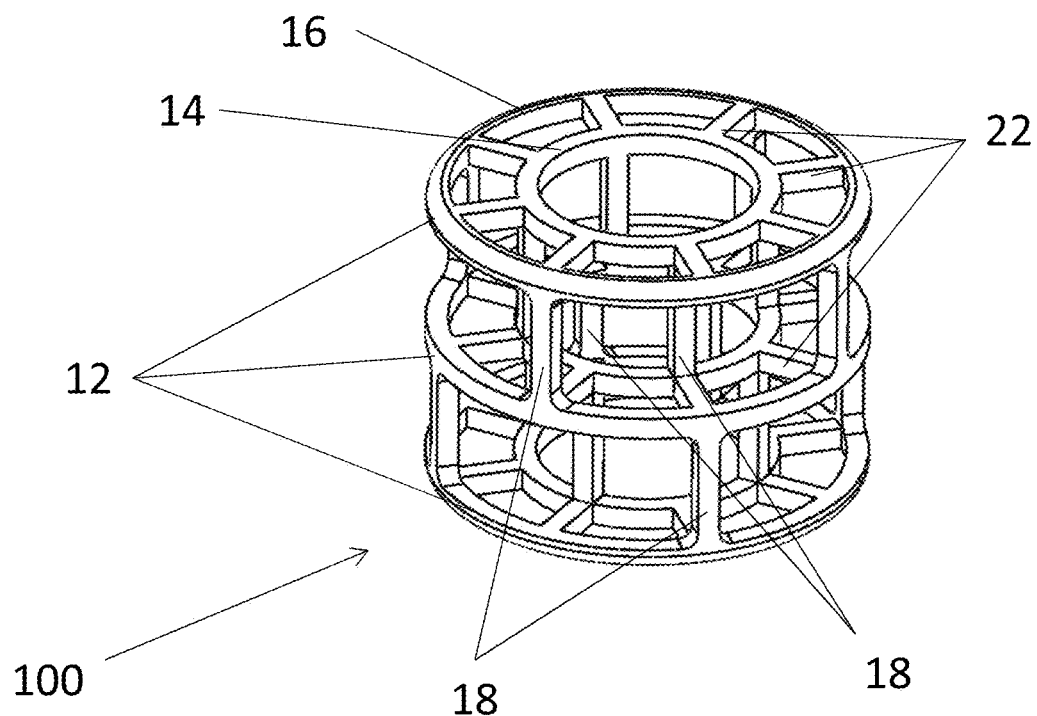
FIG. 26 is a perspective view a second embodiment of the device showing the top, front, and side.
Figure 27:
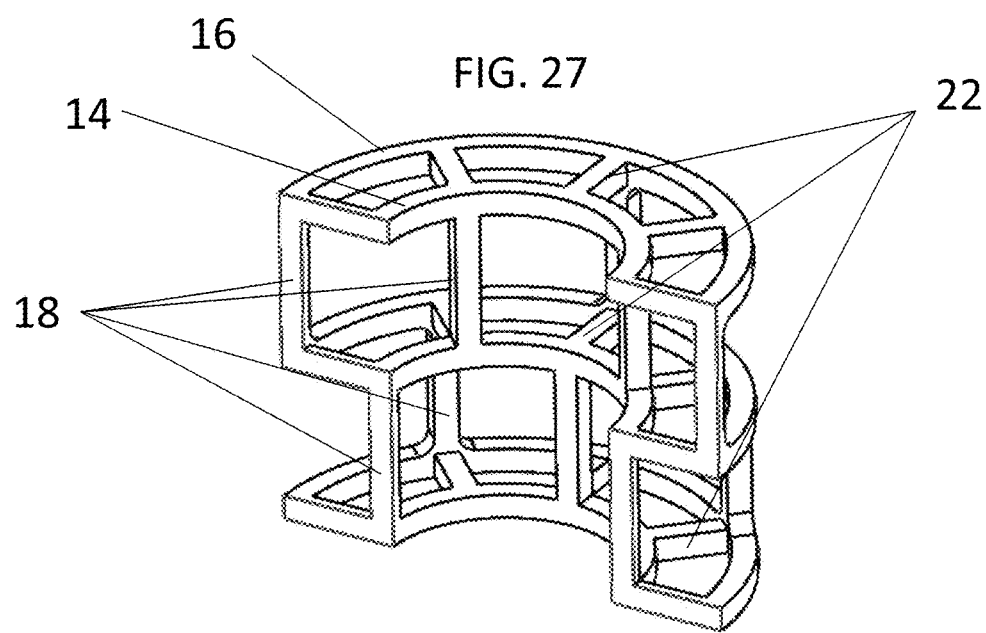
FIG. 27 is a cross-sectional view of the second embodiment.

FIGS. 26-29 illustrate a second embodiment of the device 100. This embodiment may be used with a number of different bone structures such as, for example, a mid-shaft for a long bone such as the femur or in the foot and/or ankle. FIGS. 26 and 27 illustrate the same 3-level design shown in FIGS. 1-15, albeit in a relatively cylindrical arrangement rather than the approximately rectangular cuboid with rounded corners shown in the first embodiment.

The key structure of the second embodiment is the same as in the first embodiment. More specifically, the second embodiment includes a support frame 10 that bounds and surrounds a porous architecture 50. The frame 10 includes a number of layers 12. Each layer 12 includes an inner rim 14 and an outer rim 16. The layers are connected to one another by a first set of struts 18, and the inner rims 14 and outer rims 16 are connected to one another by a second set of struts 22. The first set of struts 18 are connected to the layers 12 in an offsetting manner, which to say that the first and second layers are connected to one another by struts 18 that are attached to the outer rims 16 while the second and third layers are connected to one another by struts 18 that are attached to the inner rims 14. If viewed from the cross-sectional side view, as best shown in FIG. 27, this offsetting arraignment forms an approximate S-shape. The porous architecture 50 is the same as with the first embodiment.

Figure 28:
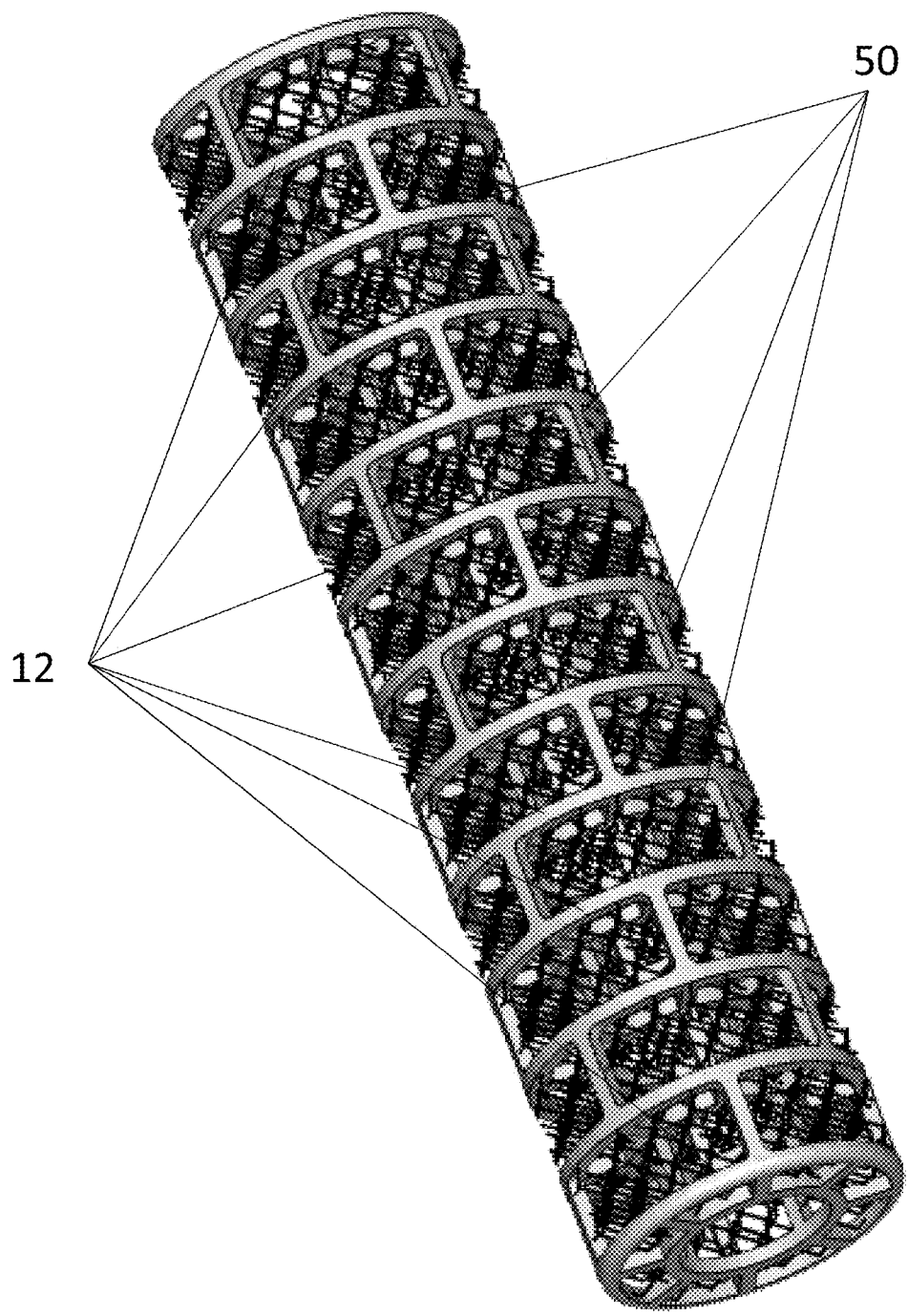
FIG. 28 is a perspective view of a larger variant of the second embodiment having a porous architecture.
Figure 29:
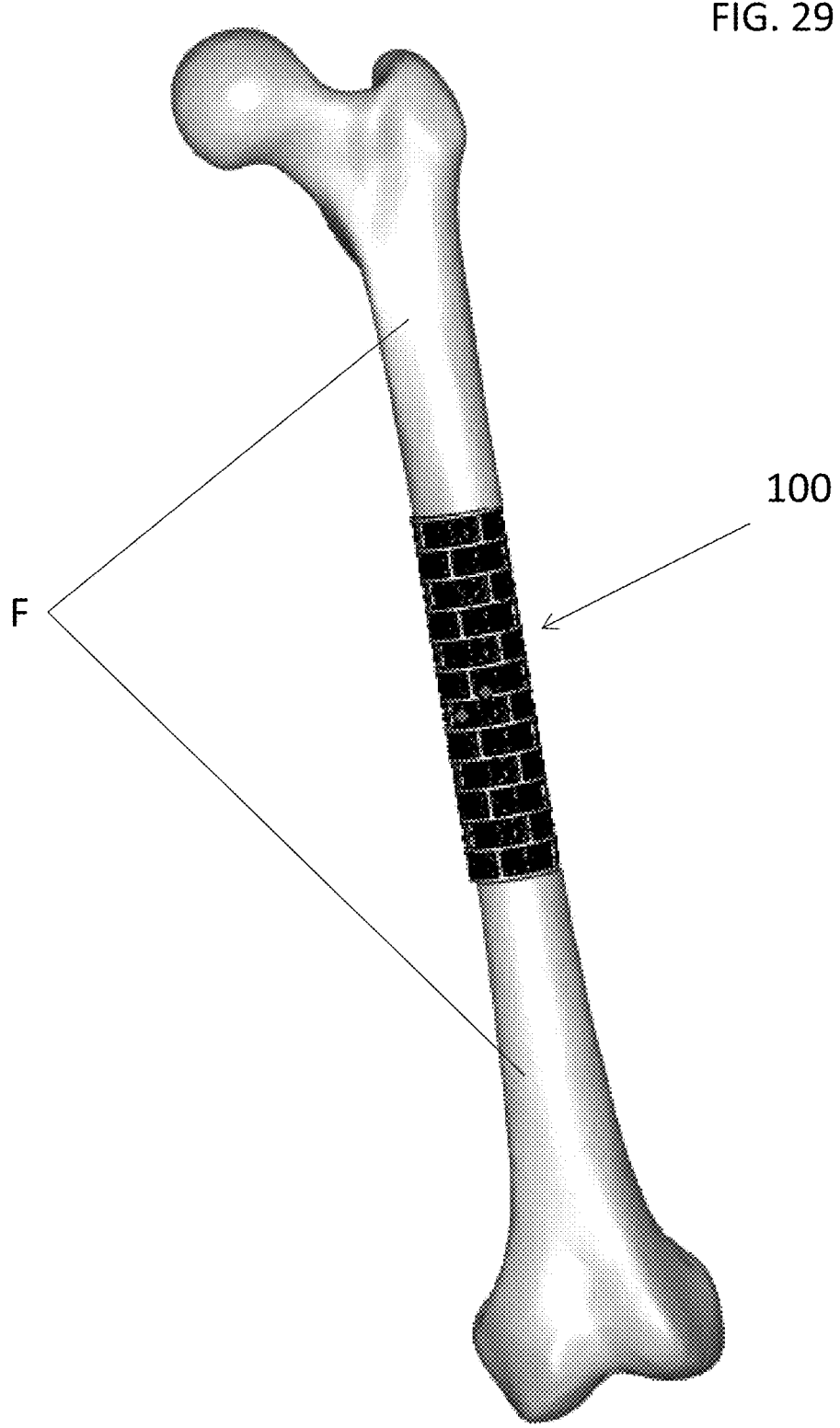
FIG. 29 illustrates the second embodiment in use a femur implant.

FIGS. 28 and 29 illustrate the use of this second embodiment as a mid-shaft insert for a long bone, such as the femur F. A longer insert is needed in this instance, and so a total of 13 layers 12 are provided. The off-setting strut arraignment is maintained throughout all 13 layers 12.

It is understood that the embodiments described herein are merely illustrative of the present invention. Variations in the construction of the Internal bone fixation device may be contemplated by one skilled in the art without limiting the intended scope of the invention herein disclosed and as defined by the following claims.

What is claimed is:

1. An internal bone fixation device comprising:
   at least three layers, each layer having an inner rim and an outer rim that are connected by one or more rim struts; in each layer the inner rim and outer rim arranged in a horizontal orientation relative to one another, and each of the layers arranged in a vertical orientation relative to one another;
   wherein the at least three layers are connected to one another by one or more layer struts;
   wherein the layer struts and rim struts are configured to connect the inner rims and outer rims and the at least three layers in an alternating pattern that forms an approximate s-shape or a reverse s-shape for every three layers, the layer struts configured to connect the layers to one another by extending in an alternating pattern between either the outer rim on one layer and between the inner rim on the next layer or between the inner rim on one layer and the outer rim on the next layer; and
   wherein at least a portion of the area between layers includes a porous architecture.

2. The device of claim 1, wherein the inner rims form an open channel.

3. The device of claim 2, wherein the at least three layers are separated from one another by approximately the same distance.

4. The device of claim 3, wherein an outer surface of the device is smoothed.

5. The device of claim 3, wherein an outer surface of the device is roughened.

6. The device of claim 1, wherein the at least three layers are an odd number of layers.

7. The device of claim 1, further including apertures for insertion of fastening devices.

8. The device of claim 1, wherein the inner rims and outer rims are approximately in the shape of a trapezoid having rounded corners.

9. The device of claim 1, wherein the inner rims and outer rims are approximately in the shape of circles.

10. The device of claim 1, wherein the porous architecture includes a plurality of openings on an outer surface area.

11. The device of claim 1, wherein the at least three layers are sized and shaped so as to be adapted for lumbar interbody fusion.

12. The device of claim 1, wherein the at least three layers are sized and shaped so as to be adapted for mid-shaft long bone fusion.

13. The device of claim 1, wherein the at least three layers are sized and shaped so as to be adapted for foot or ankle fusion.

* * * * *